United States Patent [19]

Fine

[11] 3,973,910

[45] Aug. 10, 1976

[54] METHOD OF MEASURING THE N-NITROSOAMINE CONTENT OF A SAMPLE

[75] Inventor: David H. Fine, Framingham, Mass.

[73] Assignee: Thermo Electron Corporation, Waltham, Mass.

[22] Filed: Feb. 5, 1973

[21] Appl. No.: 329,949

[52] U.S. Cl. .................. 23/230 PC; 23/230 R; 23/230 M; 23/232 R; 23/232 E; 23/253 PC; 23/254 R; 23/254 E
[51] Int. Cl.$^2$ .................. G01N 21/52; G01N 23/54; G01N 31/10
[58] Field of Search ....... 23/230 PC, 230 M, 230 R, 23/232 R, 253 R, 254 R

[56] References Cited
UNITED STATES PATENTS

| | | | |
|---|---|---|---|
| 2,395,489 | 2/1946 | Major et al. .................. | 23/232 R |
| 3,647,387 | 3/1972 | Benson et al. .................. | 23/232 R |
| 3,718,429 | 2/1973 | Williamson, Jr. .................. | 23/232 R |
| 3,746,513 | 7/1973 | Warnick et al. .................. | 23/230 PC X |

OTHER PUBLICATIONS

Open Chain Nitrogen Compounds, Smith, pp. 470–472, 508, QD 412 NIS6, vol. 2, 1966.
C. H. Bamford, J. Chem. Soc., pp. 12–17 (1939).
Eisenbrand et al., Arzneimittal–Forschung, vol. 20, pp. 1513–1517, (1970).
N–Nitrosoamides of Secondary Carbinamines; An Example of Intramolecular Inversion of Configuration, White et al., J. Am. Chem. Soc., 83, p. 1179.
The Chemistry of the N–alkyl–N–nitrosoamides, White et al., J. Am. Chem. Soc., 77, p. 6011.
N–Nitroamides and N–Nitrocarbamates–III Amino Acid Derivatives, White et al., J. Am. Chem. Soc., 29, p. 3636.
The Chemistry of the N–Alkyl–N–nitrosoamines, White, J. Am. Chem. Soc., 77, p. 6014.
Die Reaktion von $^{15}$N–markierten Organischem Nitritien RO$^{15}$NO mit Stickoyd $^{14}$NO., Kuhn et al., Hel. Chimica Acta, vol. 143, p. 607.
Problems & Progress in the Determination of Trace Quantities of Nitrosamines, Foreman et al., Inter. Sym. on Identification & Measurement of Environmental Pollutants, June 1971, pp. 190–194.

*Primary Examiner*—Morris O. Wolk
*Assistant Examiner*—Michael S. Marcus
*Attorney, Agent, or Firm*—James L. Neal

[57] ABSTRACT

The N-nitrosoamine content of a sample is measured by breaking the N—NO bond in the N-nitrosoamine molecule so as to liberate nitric oxide and thereafter measuring the amount of nitric oxide liberated.

25 Claims, 4 Drawing Figures

METHOD OF MEASURING THE N-NITROSOAMINE CONTENT OF A SAMPLE

BACKGROUND OF THE INVENTION

N-nitrosoamines are the most carcinogenic compounds presently known. A single part per million dose may suffice to produce tumors. These compounds have been found to trace quantities in many materials which are taken internally by humans, such as artificial food additives and tobacco smoke. In addition, they may be formed in vivo by internally taking the chemical precursors. In the continuing research into tumor producing substances, N-nitrosoamines are compounds which require study and for which tolerable levels of human consumption need to be determined. As of yet, such levels have not been adequately determined. This is due, at least in part, to the difficulty in measuring the quantity of N-nitrosoamine compounds in particular samples.

One prior method of N-nitrosoamine measurement is to heat the N-nitrosoamine with hydrogen to convert the nitrogen in the N-nitrosoamine to ammonia. The resulting ammonia may then be detected. The major disadvantage of this method is amines and amino acids and other nitrogen fragments are also converted to ammonia and are difficult to distinguish from the ammonia produced by the N-nitrosoamines. This problem may be partly, but only partly, overcome by prior separation on a gas chromatograph column. Even then, identification of the ammonia resulting from converted N-nitrosoamine must be confirmed by high sensitivity mass spectrometry. The results of such a process are very difficult and time consuming to obtain.

Another method which has been tried involves dissolving a sample in a solvent to which nitric oxide dyes are added. Exposure to ultra violet light produces a color change. The color change was measured to provide a reading of N-nitrosoamine content. The method provided very little success. One reason is that other materials which commonly occur in samples also produce color change and thereby erroneous readings. One such other material is furfural.

BRIEF SUMMARY OF THE INVENTION

A method for detecting the concentration of N-nitrosoamines in specific samples is provided. N-nitrosoamines have the general formula:

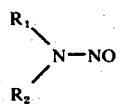

wherein $R_1$ and $R_2$ are the same or different organic radicals, including those radicals which together constitute with the non-nitroso N of the above depicted N—NO bond a nitrogen heterocyclic radical. According to this method, the N—NO bond which is generally the weakest bond, is first broken to selectively release nitric oxide and then the quantity of liberated nitric oxide is measured. The quantity of nitric oxide released is directly related to the N-nitrosoamine present. Therefore, measurement of nitric oxdie provides an immediate, accurate and direct reading of the N-nitrosoamine content of the sample.

The N—NO bond can be broken by adding to the N-nitrosoamine molecule an amount of energy just sufficient to break the N—NO bond. This energy may be maintained at a level below that sufficient to break other bonds in the molecule since the N—NO bond is, in N-nitrosoamines, the weakest bond. The N—NO bond strength is typically 5 to 12 Kcal per mole. The energization of the N-nitrosoamine molecule liberates nitric oxide according to the following reaction:

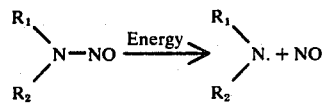

The liberated nitric oxide may be measured directly or it may be oxidized to form nitrogen dioxide and the presence of nitrogen dioxide measured by conventional techniques.

DETAILED DESCRIPTION OF THE DRAWINGS

Figure 1:
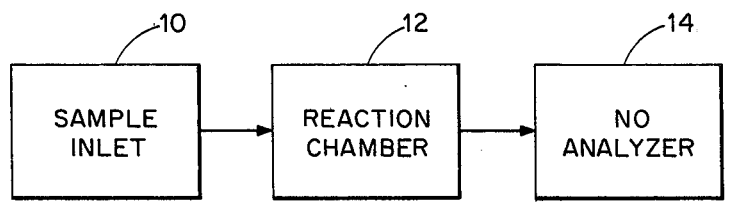
FIG. 1 is a block diagram illustrating apparatus forming the method of this invention.

The apparatus depicted in FIG. 1 comprises a sample inlet means 10, a reaction chamber 12 and a nitric oxide analyzer 14. A sample to be tested for N-nitrosoamine content is injected into the sample inlet means 10. When injected, the sample may be in a condition for immediate receipt into the reaction chamber 12 (e.g., in gaseous state) or it may be in a condition requiring specific preparation for the reaction chamber (e.g., in certain liquid or solid states). In circumstances where the sample must be prepared for the reaction chamber 12, there is incorporated with the sample inlet means 10 an appropriate sample preparing apparatus. An example of a sample preparing operation is discussed below.

The reaction chamber 12 subjects the sample to an energy level which is sufficiently high that energy added to the N-nitrosoamine molecule will break the N—NO bond. When the N—NO bond is broken nitric oxide is liberated. The nitric oxide is highly stable and has a great resistance to recombining with the remaining fragments of the N-nitrosoamine molecule, even though such fragments may be unstable and tend to rearrange into a more stable structure.

The products of the reaction chamber 12 are fed without further treatment to an appropriate nitric oxide analyzer 14. The nitric oxide analyzer produces a signal proportional to the amount of nitric oxide present and thereby also proportional to the amount of N-nitrosoamines in the sample. This method of measuring N-nitrosoamines in a sample is independent of other materials which may be present in the sample. With this invention, depending on the sensitivity of the particular nitric oxide analyzer chosen, very low N-nitrosoamine concentrations can be measured.

Figure 2:
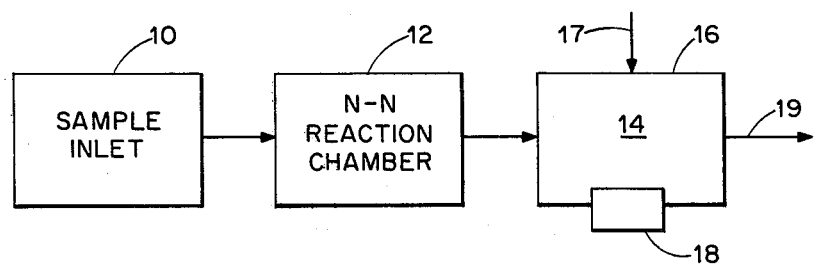
FIG. 2 is a block diagram illustrating a preferred embodiment of the apparatus of FIG. 1.

There will be described in connection with FIG. 2 a preferred embodiment of this invention wherein a solid or liquid sample containing N-nitrosoamines is to be examined. In FIGS. 1 and 2, like numerals are used to designate like parts. Briefly, from the sample inlet 10, the N-nitrosoamines containing sample is fed to the reaction chamber 12 which comprises a heated conduit for raising the temperature of the liquid sample to a temperature sufficient to break the N—NO bond and vaporize the sample. Vaporization is necessary in this embodiment in addition to the other reasons herein stated, because the analyzer includes a chemiluminescent reaction chamber 16 adapted for receipt of vaporized inputs. The output of the reaction chamber 12 is fed to the nitric oxide analyzer 14 which is of the type described in U.S. patent application Ser. No. 198,297, filed Nov. 12, 1971, in the name of David P. Lieb, entitled "Fluid Flow Control system." It incorporates the chemiluminescent reaction chamber 16, associated photosensitive device 18 and an ozone inlet 17. When materials from the reaction chamber 12 enter the reaction chamber 16, nitric oxide comes into the presence of ozone and a chemiluminescent reaction results. The intensity of the reaction is a function of the quantity of nitric oxide present. The photosensitive device 18 senses the intensity of the chemiluminescent reaction within the reaction chamber 15 and provides a signal proportional thereto. Materials are discharged from the reaction chamber 16 through an outlet 19.

Figure 4:
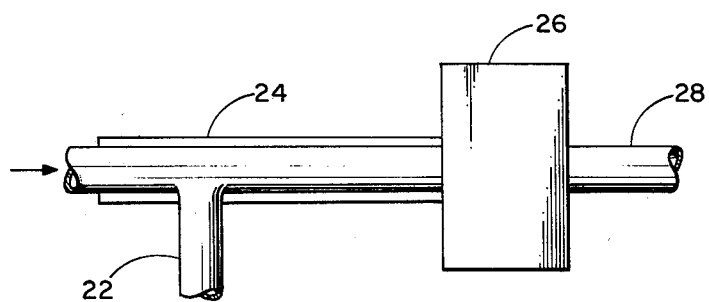
FIG. 4 is a schematic view showing apparatus for performing the method of FIG. 2.

A specific example of the operation of the invention, as depicted in FIG. 2, will be set forth in connection with FIG. 4. A liquid sample known to contain N-nitrosodiethylamine is used. The N—NO analyzer is a Model 10-A or Model 12-A NO—NOx analyzer manufactured by Thermo Electron Corporation of Waltham, Mass. The chemiluminescent reaction chamber 26 has a 6-foot long, ⅛ inch inner diameter, Grade 316 stainless steel tube leading thereto which is heated. The heated tube is represented by numeral 24 in FIG. 4 and constitutes the reaction chamber. A sample inlet port 22 is provided for admitting the sample into gases entering the heated tube 24. Tested products are exhausted from chamber 26 through a port 28. The temperature of the tube 24 is maintained between 200°C - 300°C. Residence time of 10 seconds or less is sufficient. When the sample is injected, it flash vaporizes and is transported without further treatment to the nitric oxide analyzer 26 which provides a reading of the nitric oxide present and thereby of the N-nitrodiethylamine content of the sample. This system is virtually interference free since the nitric oxide analyzer is sensitive only to nitric oxide. Ammonia and various amines which may be formed have no effect upon the reading. Additionally, extensive testing has been conducted in relation to many commonly occurring compounds which might be expected to interfere and no interference had been detected, even with test samples such as tobacco tar and chemically preserved food. For this reason, chemical clean-up of the sample, except solvent extraction in some cases, is unnecessary. With this system N-nitrosoamine concentrations from below 1 ppb on a volume-to-volume basis to pure N-nitrosoamine samples have been measured accurately. While the above temperature levels for the reaction chamber are preferred, the system will operate satisfactorily under certain conditions with a reaction temperature of 100°C to about 300°C.

Since the chemiluminescent reaction chamber 26 requires a gaseous sample, samples which are originally in a solid form and some which are in a liquid form must be prepared in such a way that the sample and the components of the system performing the method are compatible. For example, without previous chemical preparation, solid or liquid samples may be dissolved in a suitable liquid in which N-nitrosoamines are soluble. Examples of these are dichloromethane, acetone and diethylether. Dilute acids may be used as a solvent provided the N-nitrosoamines reasonably expected to be present in the sample are stable in the acid selected. After the N-nitrosoamines have been dissolved from the sample, the solvent containing the N-nitrosoamines may optionally be partially evaporated to provide a sample having desired volume and concentration characteristics. This solution is then ready for immediate introduction into the reaction chamber 12. That the solvent may also dissolve other materials is not objectionable.

Figure 3:
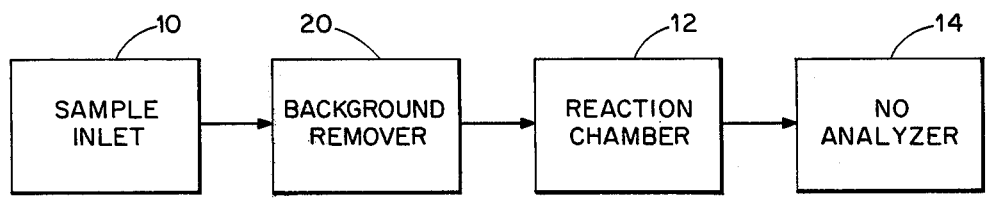
FIG. 3 is a block diagram illustrating a further embodiment of this invention.

Reference is now made to FIG. 3 wherein there is shown a sample inlet 10, a reaction chamber 12, and a nitric oxide analyzer 14, as in FIG. 1. Additionally, interposed between the sample inlet 10 and reaction chamber 12 is a background removal means 20. The background removal means 20 serves to remove nitric oxide from the sample prior to entry of sample into the reaction chamber 12. For example, if the sample entering the reaction chamber 12 is ambient air or mixed with ambient air, it may contain nitric oxide from that present in the atmosphere. If this nitric oxide is permitted to pass through the reaction chamber 12 and enter the nitric oxide analyzer 14, it will be added to nitric oxide liberated upon the breaking of N-nitrosoamine molecules. The ultimate reading will then reflect a summation of nitric oxide present from the two sources. It would then be necessary to determine the extent to which the reading reflected background nitric oxide and nitric oxide released from N-nitrosoamines. Therefore, when background nitric oxide is present, it is preferably removed prior to entry of the sample into the reaction chamber. Many techniques to remove background nitric oxide may be used. Fractional distillation and the use of chromatographic columns of various types are effective.

One suitable operation for removing background nitric oxide involves the passage of the sample, in the gaseous state through a Chromosorb column. That is, the sample is passed through a conduit filled with Chromosorb, a filtering element marketed by Perkin Elmer Corporation of Norwalk, Conn. and identified by the Model Nos. 990-5859 through 990-5889. As the fluid passes through the Chromosorb material, nitric oxide is removed. The sample may then be fed to the reaction chamber in a state free of nitric oxides. Background nitric oxide might also be removed with a molecular sieve column.

The compositions upon which the method of this invention is operable can be any having the formula appearing above. Examples of such compositions follow:

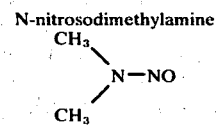

N-nitrosodimethylamine

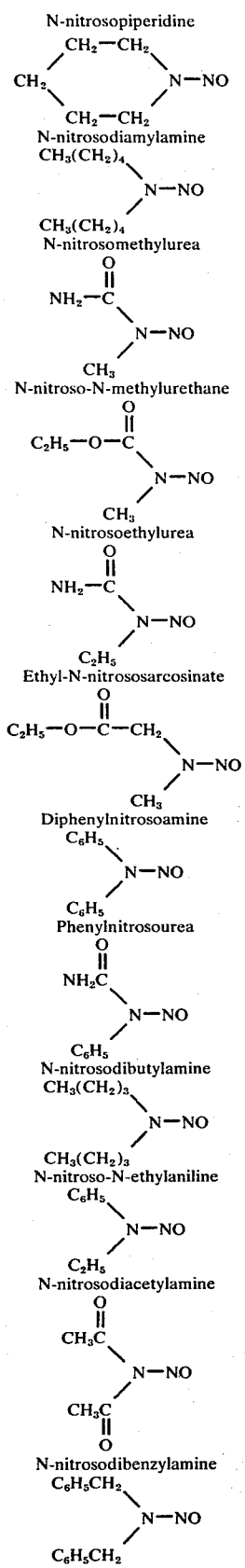

The N—NO bond is depicted above as being broken in a reaction chamber. This bond, however, may be broken in a variety of ways, at least some of them taking place in an environment which could only loosely be called a reaction chamber. For example, the N—NO bond may also be broken by subjecting the sample (i.e., the N-nitrosoamine molecule) to a high intensity electric field or to microwave energy. For example, in the case of the electric field, a field strength of 10,000 volts is sufficient; similarly, a microwave energy level of 5,680 MHz at 100 Watts is sufficient. In all cases, the intensity of the energy applied to the sample is sufficient when it is observed that nitric oxide is released.

The nitric oxide measuring steps may be by other conventional techniques as well as by the chemiluminescence technique described above. For example, the intensity to the infrared absorption spectrum of the nitric oxide liberated from the N-nitrosoamine molecule may be measured. A suitable non-dispersive infrared radiation detection instrument is available from Beckman Instruments, Inc., of Fullerton, Calif. One suitable model is designated 315-A. Further nitric oxide detection schemes may involve first oxidizing the nitric oxide to produce nitrogen dioxide and then measuring the resulting nitrogen dioxide concentration. In any event, the N-nitrosoamine content will be directly proportional to the No or $NO_2$ present. The concentration of the nitrogen dioxide may be determined by measuring the intensity of the ultra violet absorption spectrum of the nitrogen dioxide produced. An ultra violet filter photometer, Model 255-A, marketed by Beckman Instruments, Inc., of Fullerton, Calf., is suitable for this purpose.

The present invention has been described in reference to various embodiments. It should be understood that modifications may be made by those skilled in the art without departing from the scope of the invention.

What is claimed is:

1. A method of measuring the content in a sample of compounds having the general formula:

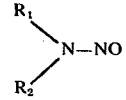

wherein $R_1$ and $R_2$ are the same or different organic radicals, including those radicals which together constitute with the non-nitroso N of the depicted N—NO bond a nitrogen heterocyclic radical, and wherein the N—NO bond is the weakest bond in the molecule, comprising the steps of:

a. heating the sample to provide an amount of thermal energy effective to break the N—NO bond and ineffective to break other molecular bonds in any substantial number for selectively liberating nitric oxide (NO), said heating step being the sole energization step for breaking molecular bonds; and b. measuring in the gaseous phase the amount of nitric oxide (NO) liberated by said heating step.

2. A method according to claim 1 wherein the amount of nitric oxide (NO) liberated is measured by:

a. reacting the nitric oxide (NO) with ozone ($O_3$); and b. measuring the intensity of the resultant chemiluminescent emission.

3. A method according to claim 1 wherein the amount of nitric oxide (NO) liberated is determined by measuring the intensity of the infrared absorption spectrum of the liberated nitric oxide (NO).

4. The method of claim 1 wherein said heating step comprises the step of flash vaporizing the sample.

5. A method according to claim 1 wherein the amount of nitric oxide (NO) liberated is determined by:
   a. oxidizing the nitric oxide (NO) to produce nitrogen dioxide ($NO_2$); and
   b. measuring the nitrogen dioxide ($NO_2$) concentration.

6. The method according to claim 5 wherein the concentration of said nitrogen dioxide ($NO_2$) is determined by measuring the intensity of the ultra violet absorption spectrum of the nitric dioxide ($NO_2$).

7. A method of measuring the content in a sample of compounds having the general formula:

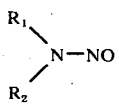

wherein $R_1$ and $R_2$ are the same or different organic radicals, including those radicals which together constitute with the non-nitroso N of the depicted N—NO bond a nitrogen heterocyclic radical, and wherein the N—NO bond is the weakest bond in the molecule, comprising the steps of:
   a. heating said sample to a temperature from 100°C to about 300°C to provide an amount of thermal energy sufficient to break the N—NO bond and insufficient to break other molecular bonds in any substantial number, said heating step being the sole energization step for breaking molecular bonds, thereby to selectively liberate nitric oxide (NO) gas; and
   b. measuring in the gaseous phase the amount of nitric oxide (NO) liberated by said heating step.

8. A method according to claim 7 in which said N—NO bond is broken by passing the sample through a heated conduit forming a reaction chamber for said sample.

9. A method according to claim 8 wherein said heating step comprises the step of injecting the sample into said reaction chamber heated to a temperature from 200°C to about 300°C.

10. A method according to claim 7 wherein said sample is non-gaseous, further comprising the steps of dissolving said sample in a liquid in which compounds having the general formula:

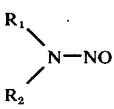

are soluble and thereafter subjecting the resulting compound containing liquid to said heating step.

11. A method according to claim 9 in which the residence time of the sample in said reaction chamber is less than 10 seconds.

12. A method of measuring the content in a sample, wherein said sample is in a gaseous form, of compounds having the general formula:

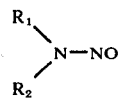

wherein $R_1$ and $R_2$ are the same or different organic radicals, including those radicals which together constitute with the non-nitroso N of the depicted N—NO bond a nitrogen heterocyclic radical, and wherein the N—NO bond is the weakest bond in the molecule, comprising the steps of:
   a. breaking the N—NO bond by heating said sample in a reaction chamber heated to a temperature from 200°C to about 300°C to cause said sample to liberate nitric oxide (NO) gas; and
   b. measuring in the gaseous phase the amount of said nitric oxide (NO) gas liberated by said breaking step by reacting said nitric oxide (NO) gas with ozone ($O_3$) gas and by measuring the intensity of the chemiluminescent emission resulting from said reaction to provide a direct and immediate measurement of the content of said compounds in said sample.

13. A method of measuring the content in a sample of compounds having the general formula:

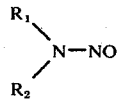

wherein $R_1$ and $R_2$ are the same or different organic radicals, including those radicals which together constitue with the non-nitroso N of the depicted N—NO bond a nitrogen heterocyclic radical, and wherein the N—NO bond is the weakest bond in the molecule, comprising the steps of:
   a. flash vaporizing the sample at a temperature from 200°C to about 300°C for approximately instantaneously breaking the N—NO bond while providing a level of thermal energy to the sample insufficient to break other molecular bonds thereby selectively liberating nitric oxide (NO) gas; and
   b. measuring in the gaseous phase the amount of nitric oxide (NO) liberated by said breaking step.

14. The method according to claim 13 wherein said measuring step comprises reacting said nitric oxide (NO) with ozone ($O_3$) and measuring the intensity of the chemiluminescent emission resulting from said reacting step.

15. A method of measuring in a sample the content of compounds selected from the group consisting of:
N-nitrosodimethylamine
N-nitrosopiperidine
N-nitrosodiamylamine
N-nitrosomethylurea
N-nitroso-N-methylurethane
N-nitrosoethylurea
Ethyl-N-nitrososarcosinate
Diphenylnitrosoamine
Phenylnitrosourea
N-nitrosodibutylamine
N-nitroso-N-ethylaniline
N-nitrosodiacetylamine
N-nitrosodibenzylamine
and mixtures thereof comprising the steps of:

a. heating the sample at a temperature from 100°C to about 300°C for providing an amount of thermal energy sufficient to break the N—NO bond and insufficient to break other molecular bonds in any substantial number, said heating step being the sole energization step for breaking molecular bonds, thereby to selectively liberate nitric oxide (NO) gas;

b. measuring in the gaseous phase the amount of nitric oxide (NO) liberated by said heating step.

16. The method according to claim 15 wherein said heating step comprises the step of flash vaporizing the sample.

17. The method according to claim 15 wherein said measuring step comprises reacting said nitric oxide (NO) with ozone ($O_3$) and measuring the intensity of the chemiluminescent emission resulting from said reacting to provide a direct and immediate measurement of the content of said compositions and said sample.

18. The method according to claim 17 wherein said heating step comprises the step of passing the sample through a heated conduit, further comprising the step of admitting the output from said heated conduit directly into a reaction chamber containing ozone.

19. A method of measuring in a sample the content of compounds selected from the group consisting of:
N-nitrosodimethylamine
N-nitrosopiperidine
N-nitrosodiamylamine
N-nitrosomethylurea
N-nitroso-N-methylurethane
N-nitrosoethylurea
Ethyl-N-nitrososarcosinate
Diphenylnitrosoamine
Phenylnitrosourea
N-nitrosodibutylamine
N-nitroso-N-ethylaniline
N-nitrosodiacetylamine
N-nitrosodibenzylamine
and mixtures thereof, comprising the steps of:
a. breaking the N—NO bond in said compounds by heating said sample to a temperature from 200°C to about 300°C for selectively liberating nitric oxide (NO); and
b. measuring in the gaseous phase the amount of said nitric oxide (NO) liberated by said breaking step by reacting said nitric oxide (NO) with ozone ($O_3$) and by measuring the intensity of the chemiluminescent emission resulting from said reaction to provide a direct and immediate measurement of the content of said compounds in said sample.

20. A method according to claim 19 in which said N—NO bond is broken by passing said sample through a heated reaction chamber.

21. A method according to claim 20 in which the residence time of the sample in said reaction chamber is less than 10 seconds.

22. A method according to claim 19 wherein said sample is non-gaseous, further comprising the step of converting said non-gaseous sample to a gaseous form prior to the measurement of said nitric oxide (NO).

23. A method according to claim 22 wherein said converting step comprises the steps of dissolving said sample in a liquid in which said compounds are soluble and injecting the resulting compound containing liquid into said heated tube to cause said sample to vaporize and to liberate said nitric oxide (NO).

24. A method of measuring the N-nitrosoamine content of a sample, wherein the N-nitrosoamines have the general formula:

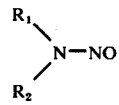

wherein $R_1$ and $R_2$ are the same or different organic radicals, including those radicals which together constitute with the non-nitroso N of the depicted N—NO bond a nitrogen heterocyclic radical, and wherein the N—NO bond is the weakest bond in the molecule, comprising the steps of:
a. breaking the N—NO bond by exposing the N-nitrosoamine molecule to a high intensity electrical field for adding to the N-nitrosoamine molecule an amount of energy sufficient to liberate the nitric oxide (NO); and
b. measuring the amount of nitric oxide liberated by said breaking step.

25. A method of measuring the N-nitrosoamine content of a sample, wherein the N-nitrosoamines have the general formula:

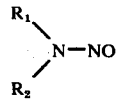

wherein $R_1$ and $R_2$ are the same or different organic radicals, including those radicals which together constitute with the non-nitroso N of the depicted N—NO bond a nitrogen heterocyclic radical, and wherein the N—NO bond is the weakest bond in the molecule, comprising the steps of:
a. breaking the N-NO bond by exposing the N-nitrosoamine molecule to microwave energy for adding to the N-nitrosoamine molecule an amount of energy sufficient to liberate the nitric oxide (NO); and
b. measuring the amount of nitric oxide (NO) liberated by said breaking step.

* * * * *